United States Patent [19]
Fujii et al.
[11] Patent Number: 4,604,234
[45] Date of Patent: Aug. 5, 1986

[54] PROTEIN HAVING CELL GROWTH STIMULATING ACTION, COMPOSITION THEREOF AND METHOD FOR PRODUCING THE SAME

[75] Inventors: Setsuro Fujii, Toyonaka; Nobumoto Chikazawa, Nara; Teruo Arima, Amagasaki; Masakazu Fukushima, Hirakata, all of Japan

[73] Assignee: Sanwa Kagaku Kenyusho Co., Ltd., Nagoya, Japan

[21] Appl. No.: 584,335

[22] Filed: Feb. 28, 1984

[30] Foreign Application Priority Data

Jun. 30, 1983 [JP] Japan ..................... 58-119863

[51] Int. Cl.[4] ..................... C07K 15/04; C12P 21/00; A61K 37/00

[52] U.S. Cl. ..................... 514/2; 435/68; 435/879; 435/884; 435/839; 435/885; 435/880; 435/849; 435/873; 435/843; 435/842; 424/145; 514/6; 530/350

[58] Field of Search ............. 260/112 R; 435/68, 170, 435/842; 424/177, 179, 289

[56] References Cited

U.S. PATENT DOCUMENTS 2,944,940 7/1960 Fischer et al. ..................... 424/179
3,243,345 3/1966 de Jager ..................... 424/179
4,014,992 3/1970 Jolles et al. ..................... 424/177
4,287,184 9/1981 Young ..................... 424/95
4,292,324 9/1981 Jönsson et al. ..................... 424/289
4,436,816 3/1984 Dinka ..................... 435/948

OTHER PUBLICATIONS

*PNAS*, vol. 68(10), 1971 Aryeletti et al., Nerve Growth Factor from Mouse Submoxillery Gland, pp. 2417-2420.

*PNAS*, vol. 70(4) 1979, Purification of Platelet Derivel Growth Factor, Antoniades et al, pp. 1809-1813.

*Physiology Review* 60(4) 1980, Physiology of Nerve Growth Factor, Thaenen et al, p. 1302.

*Primary Examiner*—J. Kight
*Assistant Examiner*—Garnette D. Draper
*Attorney, Agent, or Firm*—Stiefel, Gross, Kurland & Pavane

[57] ABSTRACT

A protein effective in stimulating cell growth activity. The protein has a molecular weight of from 5,000 to about 160,000, is composed predominantly of neutral and acidic amino acids, contains a significant amount of glutamic acid and aspartic acid, and is substantially free of nucleoside phosphotransferase. The protein is useful as wound treatment agent and as promoting agent in the synthesis of DNA. A method of producing the protein and compositions containing the same are also disclosed.

30 Claims, 1 Drawing Figure

PROTEIN HAVING CELL GROWTH STIMULATING ACTION, COMPOSITION THEREOF AND METHOD FOR PRODUCING THE SAME

BACKGROUND OF THE INVENTION (1) Field of the Invention

The invention relates to a novel protein having a cell growth stimulating activity, a composition containing said protein, and a method for producing said protein. The novel protein of this invention is useful as a wound treatment agent and a promoting agent in the synthesis of DNA.

(2) Description of the Prior Art

It has been known that a nucleoside phosphotransferase-containing fraction of broth and cells which cultured Clostridium perfringens thereon is effective as a wound treatment agent (Japanese Patent unexamined Publication No. 147908/1979). It has also been disclosed that a polypeptide, of a molecular weight of about 5,300 having 52 amino acids, isolated from mammalian body fluid (Japanese Patent unexamined Publication No. 38716/1982) and a composition containing each of the essential and semi-essential amino acids and malic acid (Japanese Patent unexamined Publication No. 80316/1982) are effective for treating wounds.

An oligosaccharide (composed of galactose and glucose) obtained by culturing certain species of organisms of the genus Bifidobacterium is also known as a cell growth factor substance (Japanese Patent unexamined Publication No. 104885/1980).

Other wound treatment agents heretofore known involve Zinc Oxide Ointment, Solcoseryl Ointment® (a deproteinized extract from young bovine whole blood), ZILDASAC® (Bendasac), Elase Ointment® (containing fibrinolysin, deoxyribonuclease, and chloramphenicol), Cartabes® (containing carbazochrom, and alkyldiaminoethylglycine hydrochloride), AD Ointment® (fortified cod-liver oil), Alkixa Ointment® (aluminum chlorohydroxyallantoinate) and Oronine Ointment® (chlorohexidine analogs).

Although effectiveness of the above ointments varies, any wound treatment agent desirably exhibits reliable and efficient granulation tissue-growing activity and epidermis-forming activity on the wounded portion. From this viewpoint, the development of improved wound treatment agents is in great demand.

The healing process of wound healing is very complicated physiologically. The process may be generally regarded as the successive development of various cells, followed by absorption of foreign matter, and the resultant destruction of bacteria and repair of the tissue.

When an incision is deep, blood from the ends of the incised blood vessels flows into the gap formed between the severed tissue to fill it up, after which a thrombus is formed to cover the fringes of the wound. The thrombus loses its liquid content within several hours and the surface dries to form a crust, which protects the wounded surface. The wound area is accompanied by inflammation, which starts with the inflow of body fluid into the wound surrounded by the thrombus. Inflammation thus initiated will cause the patient to feel a swelling pain. After a lapse of about 6 hours, various types of white blood cells will begin to move into the wounded portion to remove and break down the damaged cells, bacteria and other foreign matter. Fibroblasts in the dermis will then enter the wound to synthesize collagen fibers and other proteins to form scar tissue inside the corium. On the other hand, the epidermis (or the surface layer) will form a surface similar to the original skin before the patient was wounded. When formation of this layer is completed, the crust will peel off and the wound will be completely healed.

Although the process of the treatment of wounds has been thus clarified, drugs for wounds have not previously been sufficiently effective.

SUMMARY OF THE INVENTION

This invention comprises a development of the aforementioned Japanese Patent unexamined Publication No. 147908/1979. In the present invention, a protein substantially free of nucleoside phosphotransferase has been found to have properties that promote cell growth and multiplication.

In accordance with the present invention, there is provided a protein substantially free of nucleoside phosphotransferase and characterized by the following properties:

(a) a molecular weight of from about 5,000 to about 160,000 when obtained from a calibration curve showing a relationship between the molecular weight and the amount eluted, by means of high-performance liquid chromatography using as marker proteins: thioglobin (M.W. 670,000), bovine γ-globulin (M.W. 158,000), fowl ovoalbumin (M.W. 44,000), equine myoglobin (M.W. 17,000), and vitamin $B_{12}$ (M.W. 1,350);

(b) being composed predominantly of neutral and acidic amino acids and containing significant amounts of glutamic and aspartic acids as the acidic amino acids; and (c) having a cell growth stimulating activity.

There is also provided a method for producing a protein which comprises culturing a cell growth stimulating protein-producing strain selected from the following genera: Clostridium, Staphylococcus, Sarcina, Bacillus, Aerococcus, Streptococcus, Acinetobactor, Corynebacterium, Lactobacillus, Serratia, Escherichia, Salmonella, Proteus, Pseudomonas, Aeromonas, and Flavobacterium; and extracting and isolating the cell growth stimulating protein from the cultured organism or the cultured fluid.

PREFERRED EMBODIMENTS OF THE INVENTION

Figure 1:
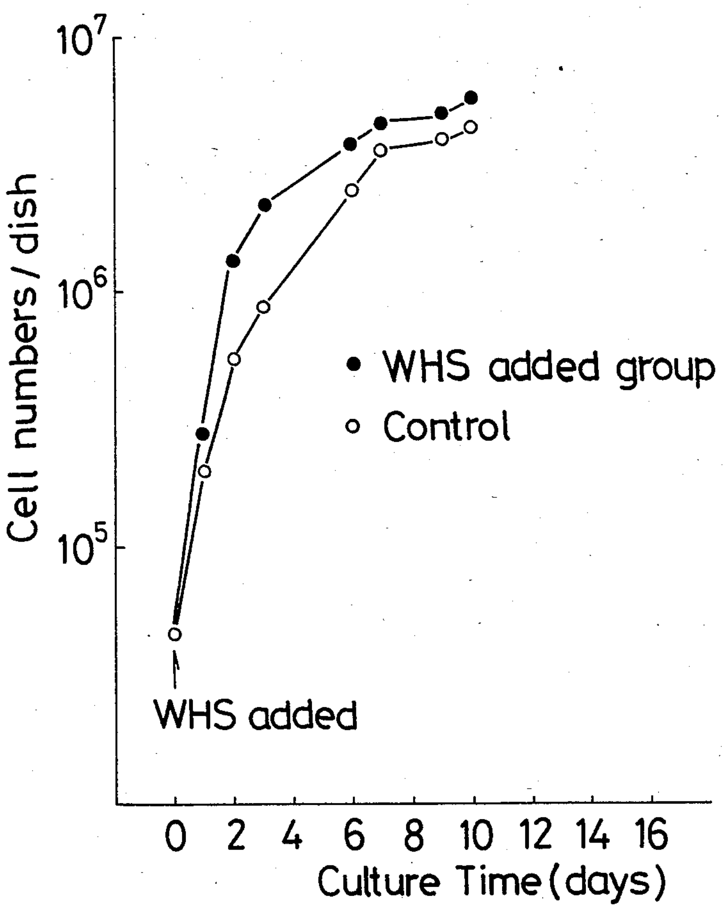
FIG. 1 is a graphical representation of the action of WHS on cell growth, in which the curve marked O shows the control group and the curve marked • shows the WHS-added group. The number of cells is plotted as ordinate, and the number of days of incubation as abscissa.

Examples of strains capable of producing the protein of the present invention are as follows:

the genus Clostridium:

*Clostridium perfringens* ATCC 21510

*Clostridium perfringens* ATCC PB6K the genus Staphylococcus:

*Staphylococcus aureus* IFO 12732

*Staphylococcus aureus* FERM P-1212

*Staphylococcus epidermidis* FERM P-7099 the genus Sarcina:

*Sarcina lutea* ATCC 9341 the genus Bacillus:

*Bacillus subtilis* FERM P-7098
the genus Aerococcus:
*Aerococcus viridans* IFO 12219
the genus Streptococcus:
*Streptococcus faecalis* ATCC 14506
the genus Acinetobactor:
*Acinetobactor calcoaceticus* IFO 12552
the genus Corynebacterium:
*Corynebacterium fascians* IFO 12077
the genus Serratia:
*Serratia marcescens* FERM P-7100
the genus Escherichia:
*Escherichia coli* FERM P-7097
the genus Salmonella:
*Salmonella enteritidis* IFO 3313
the genus Proteus:
*Proteus vulgaris* IFO 3045
*Proteus mirabilis* IFO 3849
the genus Pseudomonas:
*Pseudomonas maltophila* IFO 12020
the genus Aeromonas:
*Aeromonas hydrophila* IFO 3820
*Aeromonas hydrophilia* IFO 12978
the genus Flavobacterium:
*Flavobacterium lutescens* IFO 12997
*Flavobacterium lutescens* IFO 3085

The present invention also includes the use of any of the naturally or artificially occuring mutants of the above mentioned strains, as far as they are capable of producing the protein.

The novel protein having cell growth stimulating activity can be obtained by culturing a strain capable of producing said substance (refer to the above strains) and isolating it from the broth or cells. For instance, Clostridium perfringens ATCC 21510 is cultured on a culture medium containing a carbon source, nitrogen source, and other nutrients at preferably a pH of about 8 and a temperature of about 37° C. until it reaches the stationary phase.

Preferable examples of the culture media of the present invention are explained in the working examples as stated hereinafter.

The cell growth stimulating protein of the present invention is usually contained in large quantity in the cultured cells rather than the cultured filtrate, depending upon the kind of microorganism used. In extracting and isolating the protein, the cultured cells are, for example, treated with an ultrasonic apparatus, a homogenizer or a hypotonic solution to destroy or crush the cell walls, followed by extraction of the treated cells. The cell growth stimulating protein of the present invention is digested with difficulty by conventional proteolytic enzymes such as trypsin and "Pronase" (trypsin mixture with other proteolytic enzymes). Accordingly, it is preferable to use a suitable proteolytic enzyme during extraction and isolation thereof to digest contaminant-containing body proteins and unnecessary biologically active proteins or enzymes therefrom, thereby simplifying the purification. After treatment with the proteolytic enzyme, the extract is centrifuged to remove the cell walls and nuclei therefrom to give the supernatant.

A nucleic acid-removing agent such as protamine sulfate or streptomycin sulfate is preferably used to remove nucleic acid usually contained in the supernatant. Unnecessary materials such as the nucleic acid-removing agent, sugars, or contaminated proteins are removed by ion exchange chromatography, affinity chromatography or gel filtration. Combination of ion exchange chromatography with gel filtration is preferable. DEAE Sepharose and CM Sepharose (both prepared by Pharmacia Fine Chemicals, Sweden) are preferably used as the carriers for ion exchange chromatography.

Conventional methods may be suitably selected and utilized for the extraction and purification of the desired protein from the cultured cells or broth.

The isolated cell growth stimulating protein has the following properties:

(1) Appearance: An amorphous grayish white powder (lyophylized).

(2) Solubility: Soluble in water and insoluble in organic solvents such as methanol, ethanol, acetone, and ether.

(3) Molecular weight: from 5,000 to 160,000 (the method for determination thereof will be described below).

(4) Ultraviolet absorption spectrum: at 278 nm.

(5) Infrared absorption spectrum: Dominant absorptions at 1,300, 1,550, and 1,630 $cm^{-1}$ derived from proteins or amino acids.

(6) Color reactions for proteins: Positive to any of the Xanthoprotein, Pauli, Sakaguchi, Hunter, Sullivan, Hopkins-Cole, nitrosonaphthol, Millon, Neubauer Rhode, and Liebermann reactions.

(7) Conditions affecting deactivation: No decreased activity for a period up to 6 months in 2% sterile aqueous solution of the protein at room temperature or 25° C. No decreased activity for a period up to 2 days in 2% sterile aqueous solution of the protein at 50° C.

(8) Physical shape: An amorphous powder.

(9) Electrophoretic characteristics: Rf 0.200±0.005 of the mobility of the protein when electrophoresis is conducted for 3 hours at 8 mA per gel at a pH of 8.3 by electrophoresis containing 7.5% of polyacrylamide in the gel.

(10) pH Stability: The cell growth stimulating activity is stable at a pH of from 4 to 10.

(11) Melting Point: No melting point in the solid phase. It softens at 200° C. and then gradually darkens.

(12) Isoelectric point: Usually 5.0±0.5 with an exception of 6.6.

(13) Cell growth stimulating activity: Described below.

The proteins of the present invention have the above properties and are classified, dependent upon their molecular weights, into three groups: from about 5,000 to about 10,000, from about 10,000 to 15,000, and from 150,000 to 160,000, these groups having similar amino acid compositions.

From the standpoint of the present invention, there is provided a pharmaceutical composition containing as an active ingredient the aforementioned protein and a pharmaceutically acceptable carrier. The composition may be used where cell growth stimulation is effective in the treatment of disease, such as wounds and ulcers. (e.g., peptic and lower thigh ulcers)

The protein used for this purpose is desired to be as pure as possible. However, the impure protein containing impurities in an amount which is pharmaceutically inactive and which cause no side effects may be used.

The pharmaceutical composition is usually used in external or oral dose forms. The external dose forms are exemplified by ointments, aqueous preparations, emulsions, eye drops, and suppositories, among which the most preferable is ointments. The ointment bases may be conventional bases such as petrolatum, purified lanolin, liquid paraffin, polyethylene glycol, higher aliphatic alcohols and vegetable oils. They are prepared by conventional methods. The optimal concentration of the proteins of the present invention in these pharmaceutical preparations is, although varying with the type of the preparation, from 0.0025 to 0.025% by weight for ointments.

In the ointment of the present invention it is found that addition of a zinc compound is particularly preferable. Such ointment is effective in the treatment of wounds, the ointment exerting a healing mechanism different from that known in the art. The zinc compounds are exemplified by zinc oxide, zinc salts of fatty acids, organic acids and inorganic acids such as zinc stearate, zinc lactate, zinc acetate, zinc sulfate and zinc chloride. Particularly suited are zinc oxide, zinc salts of fatty acids such as zinc stearate, and zinc salts of organic acids such as zinc lactate and zinc acetate, among which zinc oxide and zinc salts of fatty acids are particularly preferable. For example, the appropriate ratio (by weight) of the protein of the present invention to zinc oxide is from 1:2,000 to 1:8,000. The appropriate ratio (by weight) of the protein of the present invention to zinc salts of fatty acids is from 1:400 to 1:4,000. These ointments are usually applied to the wounded portion once to several times a day.

The external composition of the present invention may contain other substances which are effective in the treatment of wounds. These substances are exemplified by adrenal cortical hormones such as hydrocortisone, prednisolone, dexamethasone, betamethasone valerate, dexamethasone valerate, triamcinolone acetonide, and fluocinolone acetonide. Such adrenal cortical hormones are effective for the treatment of wounded portions due to their antiinflammatory action, though they inhibit cell multiplication. It has been found that the combination of the protein of the present invention with the adrenal cortical hormones at least prevents the inhibition of cell multiplication, thus promoting wound healing. Accordingly, the composition in which the protein is combined with an adrenal cortical hormone is a preferable pharmaceutical preparation. The ratio (by weight) of the protein to the adrenal cortical hormone therein is usually from 1:1 to 10:1. In addition to the adrenal cortical hormone, an appropriate amount of antiinflammatory agents, antibiotics, antihistamics and the like may be added thereto. In order to improve the quality of the ointment, usual additives such as wetting agents, preservatives, antiseptics, gelling agents and like may be contained therein.

The oral pharmaceutical compositions of the present invention include tablets, powders, capsules, aqueous formulations, emulsified formulations and the like. Known arts may be used for the bases in the compositions and methods for preparing the same. When the protein of the present invention is used orally, the amount thereof, although varying with the site or size of the wound, is usually from 50 mg to 2 g, two or three times a day for adults.

The protein of the present invention may readily be placed in aqueous solution by dissolving it in about 10-fold water. The aqueous solution may be formulated into oral or external aqueous formulations, oral or external emulsified formulations, eye drops and the like.

Methods for culturing various organisms, methods for purification of the cell growth stimulating substance in the present invention from the cultured cells, and physicochemical properties thereof thus obtained are described below.

Culture of Microorganisms:

EXAMPLE 1

Culture of *Clostridium perfringens* ATCC 21510

The microorganism, stocked in a cooked meat culture medium was inoculated into 100 ml of previously autoclaved Culture Medium b (refer to "Culture Media Compositions" described below) and the inoculum was incubated at 37° C. for 18 hours under a stream of nitrogen to increase the number of the microorganisms. Forty milliliters of a suspension of the cultured microorganism was placed in a culturing flask, the contents of which were inoculated into 2 L of a previously autoclaved Culture Medium b and then cultured for 24 hours under the above anaerobic conditions to further increase the number of microorganisms. The culture medium was inoculated into a fermentation tank to culture it at 37° C. under a stream of nitrogen, the fermentation tank having previously been charged with 20 L of another Culture Medium b and having been autoclaved at 121° C. for 20 minutes and then cooled to 37° C. After the start of the culture, a portions of the culture medium were withdrawn at 1 hour intervals and the turbidity thereof was measured at 660 nm using UVIDEC 320 JAPAN SPECTROSCOPIC CO., LTD. As soon as the turbidity had become nearly constant (5 to 6 hours after the start of the culture,) the culture broth was centrifuged continuously at 8,000 xg to collect the cells. The cells thus obtained were placed in 0.9% saline solution to clean them, and the mixture was filtered to remove the culture medium components. Then acetone (previously stored at −20° C.) was added to the residue. Filtration was conducted with stirring. After the procedure was replicated, the cells were collected and then spontaneously dried at room temperature. The above procedures gave about 13 g of acetone-dried powder cells. A portion of the culture solution was sampled at the end of the cultivation for purpose of identification. The cells were identified as *Clostridium perfringens* ATCC 21510.

EXAMPLE 2

Culture of *Staphylococcus aureus* IFO 12732

The microorganism in an amount corresponding to 3 platinum loops stocked on a cooked meat culture medium, were inoculated into 100 ml of autoclaved Culture Medium e (refer to "Culture Media Compositions" described below) and incubated at 37° C. for 18 hours. Ten milliliters of the culture was inoculated into 1,000 ml of autoclaved Culture Medium e and incubate at 37° C. for 19 hours. Another Culture Medium e was placed in a 20 L fermentation tank, which was autoclaved at 121° C. for 20 min. and then cooled to 37° C. A suspension of the incubated microorganisms, 800 ml, was inoculated into the tank and cultured at 37° C. After the start of the culture, aliquots of the cultured solution were periodically withdrawn to measure the turbidity by the aforementioned method. As soon as the turbidity had become constant (23 hours after the inoculation), the culture solution was continuously centrifuged at 8,000 xg to collect the cultured cells. The cells thus obtained were suspended in 0.9% saline solution, which was filtered. After 2 L of cool acetone (stored at −20° C.) was added to the residue three times to dehydrate, giving about 17 g of acetone-dried powder cells. Immediately after the end of the cultivation, were identified as *Staphylococcus aureus* IFO 12732.

EXAMPLE 3

Culture of *Escherichia coli* FERM P-7097

The microorganism, in an amount corresponding to 2 platinum loops, cultured on a slant culture medium, was inoculated into 20 ml of autoclaved Culture Medium d, and incubated at 37° C. for 17 hours. The culture solution was transferred to another Culture Medium d, (refer to "Culture Media Composition") to incubated it at 4° C. for 4 hours. The culture solution was transferred to Culture Medium d to for incubation at 37° C. for 4 hours, and finally the culture solution was transferred to a 20 L fermentation tank, in which Culture Medium d was placed, autoclaved at 121° C. and then cooled to 37° C., initiate incubation. As soon as the cell growth rate had become constant (two hours after the incubation), microorganisms collected by the aforementioned method were acetone-dried to give 18 g of the powder cells. Immediately after the end of the cultivation the cells were identified pure Escherichia coli FERM P-7097.

EXAMPLE 4

Methods for culturing other microorganisms

Microorganisms other than the above three species were cultured by fundamentally the same method. However, as shown in table 1, the culture medium and the culturing time varied with the microorganism.

Culture media used in the present invention were as follows:

| CULTURE MEDIA | |
|---|---|
| a. SCD Culture Medium | |
| Polypeptone (Casein Peptone) | 17.0 g |
| Polypeptone S (Soybean Peptone) | 3.0 g |
| Potassium Hydrogen Phosphate | 2.5 g |
| Glucose | 2.5 g |
| Sodium Chloride | 5.0 g |
| Purified Water | Total 1,000 ml |
| pH after sterilization | 7.1-7.5 |
| b. GYPC Culture Medium | |
| Polypeptone (Casein Peptone) | 20.0 g |
| Yeast Extract | 2.5 g |
| Glucose | 5.0 g |
| Sodium Carbonate | 2.0 g |
| Cystine | 1.0 g |
| Purified Water | Total 1,000 ml |
| pH after sterilization | 8.0 |
| c. GYPC Culture Medium (containing NaCl) | |
| A culture medium in which 0.5% sodium chloride is added to Culture Medium b. | |
| pH after sterilization, 8.0. | |
| d. GYP Culture Medium | |
| Polypeptone (Casein Peptone) | 20.0 g |
| Yeast Extract | 2.5 g |
| Glucose | 5.0 g |
| Sodium Carbonate | 2.0 g |
| Purified Water | Total 1,000 ml |
| pH after sterilization | 8.0 |
| e. GYP Culture Medium (containing 1% NaCl) | |
| A culture medium in which 1% sodium chloride is added to Culture Medium b. | |
| pH after sterilization, 8.0. | |
| f. 2GYP Culture Medium | |
| Polypeptone (Casein Peptone) | 40.0 g |
| Yeast Extract | 5.0 g |
| Glucose | 10.0 g |
| Sodium Carbonate | 2.0 g |
| Purified Water | Total 1,000 ml |

-continued

| CULTURE MEDIA | |
|---|---|
| pH after sterilization | 8.0 |
| g. 2GYP Culture Medium (containing 1% NaCl) | |
| A culture medium in which 1% sodium chloride is added to Culture Medium f. | |
| pH after sterilization, 8.0. | |
| h. Trypto-soya Culture Medium | |
| Casein Peptone | 17.0 g |
| Soybean Peptone | 3.0 g |
| Sodium Chloride | 5.0 g |
| Glucose | 2.5 g |
| Potassium Hydrogen Phosphate | 2.5 g |
| Purified Water | Total 1,000 ml |
| pH after sterilization | 7.3 ± 0.1 |

The names of cells and optimum culture media and culturing time are shown in Table 1.

TABLE 1

| Bacteria | Culture media | Culture times (hrs) |
|---|---|---|
| *Clostridium perfringens* ATCC 21510 | b | 6 |
| *Clostridium perfringens* ATCC PB6K | b | 6 |
| *Staphylococcus aureus* IFO 12723 | e | 9 |
| *Staphylococcus aureus* FERM P-1212 | e | 9 |
| *Staphylococcus epidermidis* FERM P-7099 | c | 9 |
| *Sarcina lutea* ATCC 9341 | a. h | 40 |
| *Bacillus subtilis* FERM P-7098 | d | 24 |
| *Aerococcus viridans* IFO 12219 | d | 48 |
| *Streptococcus faecalis* ATCC 14506 | d | 5 |
| *Acinetobactor calcoaceticus* IFO 12552 | a | 72 |
| *Corynebacterium fascians* IFO 12077 | a. d | 8 |
| *Serratia marcescens* FERM P-7100 | d | 8 |
| *Escherichia coli* FERM P-7097 | d | 2 |
| *Salmonella enteritidis* IFO 3313 | f | 4 |
| *Proteus vulgaris* IFO 3045 | d | 8 |
| *Proteus mirabilis* IFO 3849 | f | 5 |
| *Pseudomonas maltophila* IFO 12020 | a | 216 |
| *Aeromonas hydrophila* IFO 3820 | f | 29 |
| *Aeromonas hydrophila* IFO 12978 | d | 6 |
| *Flavobacterium lutescens* IFO 12997 | d | 9 |
| *Flavobacterium lutescens* IFO 3085 | d | 9 |

Purification of cell Growth stimulating Substance:

EXAMPLE 1

Purification of a cell growth stimulating substance obtained from *Clostridium perfringens* ATCC 21510

Acetone dried powder cells, 60 g, obtained by repetition of the method described in Example 1 of "Culture of Microorganisms", were suspended in 4 L of 0.001M Tris-HCl buffer (pH 8.0), extracted at 37° C. for 2 hours with stirring, added to a solution prepared by dissolving 80 mg of Sigma Trypsin (0.8 mole/30 min. as hydrolyzing activity of Tosyl-arginine methyl ester) in 20 ml of the same buffer, and addionally treated at 37° C. for 2 hours. The mixture was centrifuged at 8,000 xg for 30 min. to obtain the supernatant. 60 ml of an aqueous solution of 5% protamine sulfate (pH 7.0) was then added to the supernatant liquid at a temperature of below 4° C., and the mixture was stirred at 4° C. for 1 hour to remove nucleic acid. The liquid was centrifuged at 8,000 xg for 30 min. at a temperature of below 4° C. and the supernatant was used as a crude extract. The extract obtained by the above procedures began to show cell growth activity.

The sample solution was passed through a DEAD-Sepharose Cl-6B column (5.0 cm×50 cm), washed with 0.02M tris-HCl buffer (pH 8.0) to attain equilibrium. Afterward, the buffer was allowed to flow into the column to collect the eluted fractions, which were named "non-adsorptive fraction". The same buffer was further passed into the column, and then the absorbance at a wavelength of 280 nm of the fraction at a point was determined. Subsequently, 0.02M Tris-HCl buffer containing 0.2M NaCl (pH 8.0) was allowed to flow into the column to collect the eluted proteins, which were named "0.2M NaCl-eluted fraction". Finally 0.02M Tris-HCl buffer containing 0.4M NaCl (pH 8.0) was allowed to flow into the column to collect the eluted proteins, which were named "0.4M NaCl-eluted fraction".

After a portion of each of the three fractions had been desalted in a dialyzing membrance, their activity was determined using BHK-21 cells according to "Determination of cell growth stimulating activity" described hereinafter. The activity was observed in the "0.2M NaCl-eluted fraction". A portion of the fraction was passed into "Sephacryl S-300 column", 2.0 cm×95 cm, to which 0.025M Tris-HCl buffer containing 0.1M NaCl was allowed to flow to carry out gel filtration. When the eluted proteins were divided into 6 fractions to determine the activity, cell growth stimulating activity was observed in fractions according to positions between thioglobin (M.W. 670,000) and γ-globulin (M.W. 158,000) and also in fractions according to a position of M.W. about 15,000. No activity was observed at a position eluting nucleoside phosphotransferase (M.W. 48,000).

Because the volume having a the fraction of M.W. about 15,000 was small, the following treatment was performed to give a purified product from fractions of higher molecular weights.

The aforementioned "0.2M NaCl-eluted fraction" was filtered with an ultrafilter using a module of an excluded 50,000 molecular weight, (available from Asahi chemical Industry Co., Ltd. of Japan). Cooled distilled water was added to the filtrate, further ultra-filtration was carried out to effect desalting, and finally the concentrate was placed in a dialyzing membrane, which was dialyzed against the distilled water at 4° C. The powder obtained by lyophilizing the contents in the membrane was named a "partially purified cell-multiplying preparation (WHS)".

About 3 g of a protein was obtained by the procedure. Because several proteins not responsible for stimulation of cell growth remained in the protein, greater purification was obtained by the following method to give a single substance.

The above 3 g portion was dissolved in 300 ml distilled water and warmed in a water bath at 40° C. for 24 hours. Afterward, the aqueous solution was concentrated by ultrafiltration with an ultrafiltering membrane of an excluded molecular weight of 50,000 (supplied by Amicon Co., Ltd.) and the concentrate was introduced through a Sephacryl S-300 (Pharmacia Fine Chemicals, Sweden) column, 4.5 cm×100 cm, previously equilibrated with 0.025M Tris-HCl buffer containing 0.1M NaCl, through which the same buffer was allowed to flow to conduct gel filtration. A cell growth stimulating protein of M.W. about 160,000 was collected. The fraction was concentrated, dialyzed against 0.02M Tris-HCl buffer (pH 8.0), and allowed to flow into a Heparin-Sepharose 4B (Pharmacia Fine Chemicals, Sweden) column, into which the buffer was allowed to flow to elute proteins. Subsequently 0.02M Tris-HCl buffer containing 0.5M NaCl (pH 8.0) was allowed to flow into the column to elute proteins bound to the column. The two fractions thus obtained were assayed for cell growth stimulating activities. The nonadsorptive fraction in which activity was found was introduced into a Lysine-Sepharose (Pharmacia Fine Chemicals, Sweden) column, (2.2 cm×25 cm) equilibrated with previously introduced 0.02M Tris-HCl buffer (pH 8.0), and 0.05M Tris-HCl buffer containing 0.5M NaCl to collect the eluted proteins. The "0.05M Tris-HCl-eluted fraction whose cell growth stimulating activity was assayed and which exhibited activity was treated with Pronase-P. Pronase-P was added to the fraction in 1/50-fold amount of the protein content and allowed to react at 37° C. for 6 hours. Immediately after the reaction, the reacted product was introduced into the aforementioned Sephacryl S-300 column, into which the same buffer was allowed to flow to conduct gel filtration, and proteins at a position corresponding to a M.W. 160,000 were collected to evaluate their cell growth stimulating activity. Because high activity was observed in the fraction, it was dialyzed against distilled water at 4° C. and then lyophilized. (The proteins will be called "preparation" hereinafter.) The preparation was tested by disk electrophoresis using polyacrylamide gel and SDS-polyacrylamide gel, showing a single band in all cases.

Determination of The Cell Growth Stimulating Properties:

Cell multiplication is usually investigated by counting the number of cells during culture by means of a microscope, counting the number using cell-counting equipment used for that purpose, or evaluated based on the number of colonies of living cells. In order to assure accuracy of the observations, the DNA (deoxyribonucleic acid) content was measured to determine the degree of cell multiplication. DNA increases with cell division and the quantity thereof is closely related to number of cells. DNA was quantified according to the method of J. M. Kissane and E. Robins (J. B. C. Vol. 233, p.p. 184–188, 1958).

Cells of a given species were placed in the wells of a 96-well tissue-culturing plate (Linbro Scientific Inc.), in the range of between 1,000 and 3,000 to each well. A culture medium prepared by adding 10% calf serum to Eagle's MEM (minimum essential medium) was placed in the above wells. The plate was pre-incubated for 24 hours. Then the cells were transplanted into the same culture medium placed in the wells of another plate to obtain a curve showing time-course cell growth, the culture medium additionally containing drugs such as WHS, epidermal growth factor, and fibroblast growth factor. Samples were withdrawn periodically and PBS (isotonic saline-containing phosphate buffer) was placed in the respective wells to wash the medium constituents. After removal of the acid soluble substances with 0.6N trichloroacetic acid, the plate was washed with ethanol several times to defat and dry it. Then it was completely dried in a desiccator, and 25 μl of 20% 3,5-diaminobenzoic acid was placed in all the 96 wells. Afterward, the plate was maintained at 60° C. for 50 min. and 375 μl of 0.5N perchloric acid solution was placed in the wells.

The fluorescence intensity of the solution in the respective wells was measured by a fluorometer at an excitation wavelength of 412 nm, slit 6 and an absorption wavelength of 505 nm, slit 10. The intensity measured was recorded by a table computer via an exclusive interface on the on-line system. The DNA contents, the average DNA contents, and the ratio of those of added group/nonadded group were simultaneously computed and recorded. The number of cells implanted was constant.

EXAMPLE 2

Purification of cell growth stimulating factor contained in *Escherichia coli* FERM P-7097

Acetone-dried cells of *Escherichia coli* FERM P-7097, 6 g, obtained by Example 3 in "Culture of Microorganisms" were suspended in 300 ml of 1 mM Tris-HCl buffer (pH 8.0) and extracted at 37° C. for 2 hours with stirring. Trypsin (Sigma Chemical Company), 8 mg, (0.08 mole/30 min. as the hydrolyzing activity of Tosyl-arginine methyl ester) dissolved in 2 ml of the same buffer was added to the extracted suspension, which was further treated with 37° C. with stirring for 2 hours. It was then centrifuged at 8,000 xg for 30 min. to separate the supernatant. A 6 ml portion of 5% aqueous protamine sulfate solution (pH 7.0) at a temperature below 4° C. and which was stirred for 1 hour to remove nucleic acid. The solution was centrifuged at 8,000 xg for 30 min. at a temperature below 4° C. and supernatant was used as a crude extract. No cell growth stimulating activity was found in the crude extract when the activity of the sample solution was determined by the method of Example 1.

The crude extract was introduced into a DEAE-Sepharose Cl-6B, 45 cm×30 cm, sufficiently equilibrated with 0.02M Tris-HCl buffer (pH 8.0), into which the same buffer was allowed to flow to collect the eluted proteins, which were called the "non-adsorptive fraction". Subsequently, 0.02M Tris-HCl buffer containing 0.2M NaCl (pH 8.0) and 0.02M Tris-HCl buffer containing 0.4M NaCl (pH 8.0) were allowed to flow in this sequence to collect the eluted proteins, the former and the latter being called the "0.2M NaCl-eluted fraction", and the "0.4M NaCl-eluted fraction" respectively. Cell growth stimulating activity was observed in the "non-adsorptive fraction". Ion exchange chromatography was found to purify the cell growth stimulating factors even when the crude extract did not have the activity.

A portion of the fraction was applied on the Sephacryl S-300 column described in Example 1 and gel-filtered to collect a product as a symmetrical chromatographic peak at a position corresponding to a M.W. of about 5,000. The "non-adsorptive fraction" was filtered with an ultrafiltering membrane of an excluded M.W. of 1,000, the filtrate was dialyzed in a dialysis membrance against distilled water at a temperature of 4° C., and lyophilized to give a purified product of about 336 mg of protein.

EXAMPLE 3

Processes for the purification of the cell growth stimulating substance using other microorganisms are basically the same as the processes described in Examples 1 and 2. The fraction having cell growth stimulating activity was purified by dividing the substance into the "non-adsorptive fraction", "0.2M NaCl-eluted fraction" and 0.4M NaCl-eluted fraction" during the ion-exchange chromatographic process.

The substance was, except for Example 1, divided into two fractions of relatively small molecular weights, ranging from 10,000 to 15,000 and from 5,000 to 10,000. Therefore, purification was carried out using an ultrafiltering membrane of an excluded M.W. of 5,000 for the former fraction and that of an excluded M.W. of 1,000 for the latter. Cell growth stimulating fractions examined in accordance with this example are shown in Table 2, using the symbol ○.

TABLE 2

Screening of cell-growth stimulating substances from microorganisms

| | Effects on BHK-21 cells | | | | |
|---|---|---|---|---|---|
| | | | DEAE-Sepharose Column | | |
| Bacteria | Extraction | Trypsin treatment | non-absorbed | 0.2 M NaCl | 0.4 M NaCl |
| *Clostridium perfringens* ATCC 21510 | | ○ | | ○ | |
| *Clostridium perfringens* ATCC PB6K | | ○ | ○ | | |
| *Staphylococcus aureus* IFO 12732 | ○ | ○ | | ○ | |
| *Staphylococcus aureus* FERM P-1212 | ○ | ○ | ○ | | |
| *Staphylococcus epidermidis* FERM P-7099 | | ○ | | ○ | |
| *Sarcina lutea* ATCC 9341 | | ○ | | ○ | |
| *Bacillus subtilis* FERM P-7098 | | ○ | ○ | ○ | |
| *Aerococcus viridans* IFO 12219 | | ○ | | ○ | |
| *Streptococcus faecalis* ATCC 14506 | | | ○ | | |
| *Acinetobacter calcoaceticus* IFO 12552 | | | ○ | | |
| *Corynebacterium fascians* IFO 12077 | | | ○ | ○ | |
| *Serratia marcescens* FERM P-7100 | ○ | ○ | ○ | | |
| *Escherichia coli* FERM P-7097 | | | ○ | | |
| *Salmonella enteritidis* IFO 3313 | | | ○ | | |
| *Proteus vulgalis* IFO 3045 | | ○ | ○ | | |
| *Proteus mirabilis* IFO 3849 | | | ○ | | |
| *Pseudomonas maltophila* IFO 12020 | | ○ | | | ○ |
| *Aeromonas hydrophila* IFO 3820 | | | ○ | | |
| *Aeromonas hydrophila* IFO 12978 | | | ○ | | |
| *Flavobacterium lutescens* IFO 12997 | | | | | ○ |
| *Flavobacterium lutescens* IFO 3085 | | | | | ○ |

○ ; stimulative effect

Physicochemical Properties:

EXAMPLE 1

The cell growth stimulating substance of Clostridium perfringens ATCC 21510

(1) Molecular weight

The preparation (refer to "Purification of cell growth stimulating substance") was dissolved in 0.05M potassium phosphate buffer containing 0.1M NaCl (pH 6.8) at a concentration of 1%. The solution was gel-filtered through an AQUAPORE OH-300 column, 7.5 mm×600 mm, Brown Lee Inc. USA, with the same buffer allowed to flow thereinto, and the eluate was submitted to TRIROTAR II, high performance liquid chromatography, Japan Spectroscopic Co., Ltd. to obtain the amount eluted. In addition, 0.1% mixtures of each of thioglobin (M.W. 670,000), γ-globulin (M.W. 158,000), ovoalbumin (M.W. 44,000) myoglobulin (M.W. 17,000), and vitamin $B_{12}$ (M.W. 1,350) were gel-filtered under the same condition. Dependent upon the above results, a calibration curve showing the relationship between the respective amounts eluted and molecular weight was prepared. Based on the calibration curve, the M.W. of the sample was found to be 160,000.

The preparation dissolved in distilled water of 1 mg/ml concentration was serially diluted to ×2, ×4, ×8 and ×16 and was submitted to electrophoresis of 7.5% polyacrylamide containing SDS according to the Davis method (1964). 0.1M sodium phosphate buffer containing 0.1% SDS (pH 7.4) was used for the electrophoresis, which was carried out by allowing 8 mA of current per each gels flow for 4 hours. Each of the gel was then dyed with Coomassie Brilliant Blue G and spontaneously decolorized with an aqueous solution of 7.5% acetic acid and 5% methanol. Subsequently, mobility up to the dyed band was determined for the decolorized gel and γ-globlin (M.W. 160,000), bovine serum albumin (M.W. 67,000) ovoalbumin (M.W. 47,000), chymotrypsinogen (M.W. 25,000) and cytochrom C (M.W. 12,400) submitted to electrophoresis under the same conditions. A calibration curve showing the relationship between the mobility and the molecular weight was prepared, the molecular weight of the preparation being 53,000.

(2) Isoelectric point

The preparation was subjected to electrophoresis using an LKB Isoelectric Electrophoresis Apparatus according to a method described by A. Winter et al. Ampholine having a pH of 3.0 to 10 and Sephadex G-75 were used for the pH gradient-forming reagent and the supporting carrier, respectively. The former was homogenously mixed with the latter to produce a gel, into which the preparation was placed. The mixture was submitted to electrophoresis for 16 hours by allowing 15 mA of current to flow at 4° C. The gel was divided into 30 fractions and pH values were measured for the respective fractions, from which proteins were extracted. The cell growth stimulating activity was observed at a pH of 5.0±0.1.

(3) Amino acid composition

One milligram of the preparation was placed in a 5 ml ampule for hydrolysis. Re-distilled 6N HCl was added to the ampule, which was sealed while completely degassing it. Hydrolysis was carried out by keeping the ampule at 110°±1° C. for 24 hours to prepare a sample, which was determined for the amino acid contents by an Irica Kogyo Amino Acid Analyzer.

TABLE 3

Amino acid composition of cell growth stimulating substance (molecular weight 160,000) from *Clostridium perfringens* ATCC 21510

| Amino acids | μmol/mg pro. | mol/M |
|---|---|---|
| Aspartic acid | 0.686 | 109.80 |
| Threonine | 0.252 | 40.39 |
| Serine | 0.285 | 45.59 |
| Glutamic acid | 0.601 | 96.18 |
| Glycine | 0.448 | 71.66 |
| Alanine | 0.461 | 73.69 |
| Cystine | 0.018 | 2.92 |

TABLE 3-continued

Amino acid composition of cell growth stimulating substance (molecular weight 160,000) from *Clostridium perfringens* ATCC 21510

| Amino acids | μmol/mg pro. | mol/M |
|---|---|---|
| Valine | 0.456 | 73.01 |
| Methionine | 0.103 | 16.56 |
| Isoleucine | 0.342 | 54.64 |
| Leucine | 0.409 | 65.42 |
| Tyrosine | 0.339 | 54.29 |
| Phenylalanine | 0.171 | 27.43 |
| Lysine | 0.473 | 75.66 |
| Histidine | 0.066 | 10.48 |
| Arginine | 0.134 | 21.37 |
| Proline | 0.203 | 32.55 |
| Tryptophan | 0.021 | 3.36 |
| Total | 5.469 | 875.01 |

Another 1 mg portion of the preparation was placed in the 5 ml ampule, 1 ml of 5N KOH solution was added, and the ampule was sealed while blowing argon gas. Hydrolysis was carried out by keeping the ampule at 120°±1° C. for 10 hours to determine the contents of tryptophane in the preparation, employing the method of Basha et al. (1977). (Table 3 shows the results.)

The preparation was composed of about 875 amino acids, among which neutral and acidic amino acids were rich and basic amino acids were poor. The preparation was protein rich in asparagine or aspartic acid, glutamine or glutamic acid, glycine, alanine, and valine among neutral and acidic amino acids.

(4) Electrophoretic characteristics

A gel having a pH of 8.3 containing 7.5% polyacrylamide was prepared according to the method of Davis. A sampling gel containing 50 μg of the preparation was polymerized by superimposing it on the abovementioned gel, to which 2 mA of current was applied using 0.1M glycine-NaCl buffer (pH 8.3) as the electrophoretic solution to carry out electrophoresis for 3 hours. The gel was removed and dyed in a 1% Amideblack solution for 1 hour and then immersed in 7% acetic acid to spontaneously decolor it.

The pre-drying length of the gel, the lengths of the post-drying and the post-decolored gel, and the length up to the protein-dyed band were measured. The electromobility of the substance was 0.200±0.005 based on the lengths.

(5) Other characteristics

I. Appearance: An amorphous light-grayish white powder (lyophilized).

II. Solubility: Soluble in water and insoluble in organic solvents such as methanol, ethanol, acetone and ether.

III. Ultraviolet absorption spectrum: 278 nm.

IV. Ultrared absorption spectrum: Absorption at 1300, 1550 and 1630 $cm^{-1}$ derived from proteins or amino acids.

V. Color reactions: Positive to any of the Xanthoprotein, Pauli, Sakaguchi, Hunter, Sullivan, Hopkins-Cole, nitrosonaphthol, Millon, Neubauer-Road, and Liebermann reactions.

EXAMPLE 2

Cell growth stimulating substances from other organisms (1) Molecular weight Table 4 shows the estimated molecular weights of cell growth stimulating substances obtained from the respective organisms according to the method described in Example 1. From the results, the substances were divided into two groups: a substance having a M.W. of from 10,000 to 15,000, and a substance having a M.W. of from 5,000 to 10,000.

(2) Amino acid composition

The amino acid compositions of the respective substances were investigated according to the same method as described in Example 1. (The results are shown in Table 5). All of the substances were proteins rich in neutral and acidic amino acids and poor in basic amino acids. The former are proteins containing asparagine or aspartic acid, glutamine or glutamic acid, glycine, alanine, and valine in large amounts and cystine in small amounts.

TABLE 5

Amino acid composition of cell growth stimulating substances from microorganisms

| Amino acids | contents of amino acid (mol/M) (1) | (2) | (3) | (4) | (5) | (6) | (7) | (8) | (9) | (10) | (11) | (12) | (13) | (14) | (15) |
|---|---|---|---|---|---|---|---|---|---|---|---|---|---|---|---|
| Aspartic acid | 14.33 | 12.11 | 12.30 | 12.58 | 5.66 | 18.78 | 9.28 | 13.62 | 7.02 | 9.65 | 13.12 | 4.66 | 4.25 | 5.30 | 7.10 |
| Threonine | 3.76 | 5.69 | 4.60 | 5.29 | 2.32 | 7.72 | 4.42 | 6.63 | 4.36 | 5.00 | 7.03 | 2.20 | 2.61 | 3.04 | 3.43 |
| Serine | 3.33 | 5.14 | 4.95 | 5.57 | 2.19 | 11.45 | 4.97 | 6.78 | 4.27 | 4.56 | 6.33 | 2.01 | 2.08 | 2.95 | 3.28 |
| Glutamic acid | 21.35 | 15.77 | 19.97 | 14.18 | 7.04 | 43.08 | 12.98 | 18.39 | 12.49 | 12.36 | 18.50 | 6.04 | 4.76 | 7.31 | 9.53 |
| Glycine | 6.72 | 10.04 | 8.40 | 11.78 | 3.74 | 11.21 | 6.49 | 8.39 | 5.72 | 6.71 | 11.59 | 4.50 | 3.68 | 6.13 | 4.72 |
| Alanine | 6.62 | 11.96 | 8.82 | 10.10 | 3.51 | 14.68 | 7.86 | 11.35 | 18.09 | 8.07 | 12.23 | 5.84 | 4.47 | 6.68 | 6.21 |
| Cystine | 0.40 | 0.37 | — | 0.00 | 0.00 | 0.00 | 0.09 | 0.00 | 0.00 | 0.00 | 0.00 | 0.00 | 0.00 | 0.05 | 0.05 |
| Valine | 7.98 | 8.97 | 6.68 | 7.27 | 3.05 | 12.16 | 5.99 | 8.27 | 5.69 | 6.43 | 8.94 | 3.74 | 3.30 | 4.81 | 4.22 |
| Methionine | 2.25 | 2.73 | 1.49 | 2.21 | 0.79 | 2.86 | 1.75 | 2.33 | 1.19 | 1.46 | 2.48 | 0.86 | 0.91 | 1.46 | 1.40 |
| Isoleucine | 6.73 | 7.97 | 5.73 | 5.46 | 2.58 | 6.77 | 4.72 | 6.73 | 3.79 | 3.98 | 6.60 | 2.36 | 2.34 | 3.26 | 3.51 |
| Leucine | 6.28 | 8.70 | 4.97 | 6.00 | 2.70 | 6.71 | 5.75 | 7.13 | 4.32 | 5.51 | 8.13 | 3.11 | 3.11 | 4.57 | 4.33 |
| Tyrosine | 3.17 | 2.32 | 1.79 | 0.62 | 0.91 | 1.62 | 2.08 | 2.63 | 1.89 | 0.85 | 2.59 | 0.39 | 0.70 | 1.04 | 1.21 |
| Phenylalanine | 3.20 | 3.11 | 1.95 | 2.47 | 1.46 | 3.28 | 2.48 | 3.43 | 1.57 | 1.75 | 3.44 | 0.79 | 1.15 | 1.98 | 1.78 |
| Lysine | 3.42 | 8.80 | 4.53 | 8.95 | 2.22 | 5.47 | 4.14 | 5.17 | 7.60 | 6.13 | 5.63 | 2.60 | 2.75 | 4.22 | 3.05 |
| Histidine | 1.14 | 0.76 | 1.04 | 1.16 | 0.60 | 1.36 | 1.35 | 1.46 | 0.83 | 1.19 | 1.78 | 0.54 | 0.72 | 1.33 | 0.93 |
| Arginine | 0.92 | 2.80 | 0.80 | 1.84 | 0.65 | 1.72 | 1.45 | 2.33 | 1.45 | 3.52 | 1.36 | 1.13 | 1.32 | 4.83 | 0.78 |
| Proline | 3.60 | 5.37 | 4.44 | 4.82 | 1.42 | 12.69 | 3.35 | 4.27 | 3.19 | 4.33 | 5.40 | 2.69 | 2.72 | 3.18 | 2.63 |
| Tryptophan | 0.70 | 0.47 | 0.63 | 0.32 | 0.26 | 0.56 | 0.61 | 0.53 | 0.25 | 0.39 | 0.60 | 0.50 | 0.29 | 0.54 | 0.47 |
| Total | 95.90 | 113.09 | 93.09 | 100.62 | 41.11 | 162.11 | 79.75 | 109.44 | 83.72 | 81.90 | 115.76 | 43.97 | 41.16 | 62.68 | 58.62 |

(1) *Clostridium perfringens* ATCC 21510 (M.W. 15,000)
(2) *Clostridium perfringens* ATCC PB6K
(3) *Staphylococcus aureus* IFO 12732
(4) *Staphylococcus aureus* FERM P-1212
(5) *Staphylococcus epidermidis* FERM P-7099
(6) *Sarcina lutea* ATCC 9341
(7) *Bacillus subtilis* FERM P-7098
(8) *Aerococcus viridans* IFO 12219
(9) *Streptococcus faecalis* ATCC 14506
(10) *Acinetobacter calcoaceticus* IFO 12552
(11) *Corynebacterium fascians* IFO 12077
(12) *Serratia marcescens* FERM P-7100
(13) *Escherichia coli* FERM P-7097
(14) *Slamonella enteritidis* IFO 3313
(15) *Proteus vulgaris* IFO 3045

(3) Isolectric points

The isoelectric points of the respective substances were investigated according to the same method as described in Example 1. (Table 6 shows the results.) The isoelectric points of the substances are, although varying with the respective substances, found in acidic pH values within the range of the investigation.

TABLE 4

Molecular weight estimation of cell-growth stimulating substances from microorganisms.

| Bacteria | Molecular weight |
|---|---|
| *Clostridium perfringens* ATCC 21510 | 160,000–15,000 |
| *Clostridium perfringens* ATCC PB6K | 12,000–6,000 |
| *Staphylococcus aureus* IFO 12732 | 15,000 |
| *Staphylococcus aureus* FERM P-1212 | 15,000 |
| *Staphylococcus epidermidis* FERM P-7099 | 6,000–5,000 |
| *Sarcina lutea* ATCC 9341 | 15,000 |
| *Bacillus subtilis* FERM P-7098 | 10,000–5,000 |
| *Aerococcus viridans* IFO 12219 | 15,000 |
| *Streptococcus faecalis* ATCC 14506 | 10,000–5,000 |
| *Acinetobacter calcoaceticus* IFO 12552 | 15,000 |
| *Corynebacterium fascians* IFO 12077 | 15,000 |

TABLE 4-continued

Molecular weight estimation of cell-growth stimulating substances from microorganisms.

| Bacteria | Molecular weight |
|---|---|
| *Serratia marcescens* FERM P-7100 | 9,000 |
| *Escherichia coli* FERM P-7097 | 5,000 |
| *Salmonella enteritidis* IFO 3313 | 9,000–7,000 |
| *Proteus vulgaris* IFO 3045 | 8,000–5,000 |
| *Proteus mirabilis* IFO 3849 | 15,000 |
| *Pseudomonas maltophila* IFO 12020 | 15,000 |
| *Aeromonas hydrophila* IFO 3820 | 9,000 |
| *Aeromonas hydrophila* IFO 12978 | 5,000 |
| *Flavobacterium lutescens* IFO 12997 | 15,000 |
| *Flavobacterium lutescens* IFO 3085 | 15,000 |

TABLE 6

Isoelectric point of cell growth stimulating substances from microorganisms

| Bacteria | pI |
|---|---|
| *Clostridium perfringens* ATCC PB6K | 6.6 |
| *Staphylococcus aureus* IFO 12732 | 4.3 ± 0.3 |
| *Staphylococcus epidermidis* FERM P-7099 | 4.8 ± 0.4 |
| *Bacillus subtilis* FERM P-7098 | 4.7 ± 0.5 |
| *Aerococcus viridans* IFO 12219 | 4.5 ± 0.5 |
| *Streptococcus faecalis* ATCC 14506 | 4.5 ± 0.5 |
| *Acinetobacter calcoaceticus* IFO 12552 | 5.0 ± 0.5 |
| *Corynebacterium fascians* IFO 12077 | 4.6 ± 0.4 |
| *Serratia marcescens* FERM P-7100 | 5.1 ± 0.2 |
| *Proteus vulgaris* IFO 3045 | 4.5 ± 0.5 |
| *Pseudomonas maltophila* IFO 12020 | 5.0 ± 0.5 |
| *Aeromonas hydrophila* IFO 3820 | 5.1 ± 0.2 |

The pharmacological activity of the cell growth stimulating substance of the present invention is described below. The following tests employed herein were made of partially purified preparation (WHS) described in Example 1 of "Purification of cell growth stimulating substance".

(1) Fibroblast growth stimulating activity

The substance in the present invention has a cell growth stimulating activity against tissue cells from various animals (the dermal tissue, lunge, and kidney of human and the primary culture cells and strained cells of rat, mouse and hamster). The activity, as shown in FIG. 1, shortened the average cell generation time when WHS was added to conventional tissue-culturing media such as Eagle's MEM culture medium (Nissui) added with from 1% to 10% calf serum.

No method for representing the activity is available even with well known growth factors such as an epidermal growth factor, a fibroblast growth factor, and a platelet derivative growth factor used herein. Chung-Ho Chen and Sumi C. Chen (Exp. Cell Res., 136, 43) proposed a method for representing it. The inventors applied their methods to represent the activity. As shown in FIG. 1, a difference was found between the controls and the substance of the present invention during the logarithmic phase. The difference can be represented by either the amount stimulating cell growth or the shortened hours of the average generation time.

The inventors represented the amount of cell growth as the amount of DNA for enabling more quantitative expression of the activity. As described above, we determined the amount of DNA in cells because of a close relationship between the number of cells and the amount of cells, time course for determining the number of cells, and possible measurement errors in treating numerous samples at a definite point.

In order to make a general determination of the efficacy of the substance of the present invention, strained BHK-21 cells and clone 13 (hamster renal fibroblasts) were selected. The medium for culturing the cells employed herein was Eagle's MEM containing 1% calf serum for culturing the cells. The method may be carried out by using a given medium for the purpose.

Into each well of a 96-well microplate, 1500 cells accurately counted were seeded with an automatic multipipette and incubated in a 10% calf serum-containing Eagle's MEM at 37° C. for 24 hours in the presence of a mixture of 5% $CO_2$ and 95% air. After incubation, the cells were transplanted into a 10% calf serum-containing Eagle's MEM and additionally containing the substance of the present invention to prepare a time-course cell growth curve. In the case of BHK-21 cells, a distinct difference in cell growth was observed between the protein-added group from the start, and a protein-free control group 24, 48, 75 hours after the start of incubation. The difference corresponded to the difference in the concentration of the protein added but was minimal at concentrations exceeding a definite limit.

The ratio of the growth rate of the protein-added group to the protein-free group was found to hold for the Michaelis-Menten equation when a kinetic equation was applied to the relationship between the enzyme and a substitute in an enzyme reaction. Accordingly, the concept of the specific growth rate described by J. Monod (Ann. Review of Microbial., 3, 371 (1941)) was introduced into the expression of effectiveness of the protein of the present invention. The ratio of the theoretical maximum cell count in the protein-added group to that in the control is expressed by $R_{max}$ (corresponding to $V_{max}$ in the enxyme reaction).

The value equivalent to one-half the $R_{max}$ is expressed by the pharmacological concentration $K_s$ (corresponding to $K_m$ in the enzyme reaction). The Hofstee plot was applied to the calculation of the $R_{max}$ and $K_s$, thus enabling the expression of effectiveness of the protein in the present invention. If $R_{max}$ is 2, the number of cells in the protein-added group would be twice that in the control group. The smaller the concentration of the protein in the present invention required to display the effectiveness equivalent to $\frac{1}{2}$ of $R_{max}$, the larger the effectiveness, and the larger the value of $K_s$, the smaller the effectiveness. The nearer to 1 the value of $R_{max}$ is, the weaker the cell growth stimulating activity.

(2) Effects of human epidermal cells

It has previously been reported that cholera toxin has marked stimulating activity on epidermal cell growth (H. Green; Cell, 15, pp 801-811 (1978)). According to the report, effectiveness of cholera toxin was marked when the number of cells was small or when cell activity was weak. When the material of the epidermal tissues is minimal, therefore, addition of cholera toxin is effective. Simultaneous collagen-treatment of the bottom of an incubator prevents epidermal cells from being removed from the incubator, making cell multiplication advantageous.

The substance of the present invention was added simultaneously with cholera toxin to the medium for culturing human epidermal cells. When the substance was present, much stronger cell growth stimulating activity was observed than in the absence of the substance. The effective concentration of the protein was 25 μg/ml at that time, whereas an inhibitory effect was observed when 250 μg/ml of the protein was added to the medium because the epidermal cells were removed from the bottom of the incubator due to cell-coagulating action.

Cell growth stimulating activity because of the substance was observed when cholera toxin was added to the medium only in the case of inoculation of the epidermal cells; in that instance the medium was replaced by a medium containing the substance of the present invention about 1 day later. Activity was also found from inoculation when the medium containing the substance but not cholera toxin was used for culturing.

(3) Comparison of the substance of the present invention with known growth factors Growth factors presently known include epidermal growth factor (EGF), fibroblast growth factor (FGF), platelet derivative growth factor (PDGF) and nerve growth factor. WHS of the present invention was compared with the above factors.

BHK-21 cells (hamster renal fibroblasts) were used for the tests. The above factors were added to Eagle's MEM containing 10% calf serum at 37° C. under an atmosphere of a 5% $CO_2$–95% air mixture for incubating the cells and the time-course numbers of the cells were counted. EGF, FGF and PDGF increased the saturation density of the cells, whereas WHS accelerated the cell logarithmic phase but did not increase the saturation density.

The generation time of the BHK-21 cells was 15–16 hours in the absence of WHS but was shortened to 10–11 hours in the presence of WHS. It was clarified that the activity exerted at the $G_1$-stage shortened the S-stage during the course of cell division and multiplication.

WHS thus did not increase the amount of cells but promoted the cell growth speed.

(4) Effects of WHS in regenerating rat hepatic cells

Induction of various enzymes responsible for the synthesis of DNA in the growth of cells is clarified by G. Weber et al., and the fact has been verified by the regenerating rat liver as an experimental animal model. The liver of an adult rat is an organ which has terminated the syntheses of RNA, DNA and protein. Partial hepatectmized rat liver will regenerate the remaining liver, thus initiating DNA synthesis and stimulating the activity of various DNA-synthesizing enzymes.

Although WHS has been found to stimulate in vitro cell growth, we examined whether WHS has in vitro action using rat regenerated liver models.

EXPERIMENT 1

One ml of 0.02–0.05% solution of WHS, previously dissolved in isotonic saline and sterilized by filtration, was injected intraperitoneally into groups of five SPF-Wistar strain male rats, weighing 150 g, under sterile conditions. One ml of isotonic saline was injected into 5 animal control groups under similar conditions. Twelve hours after injection, these rats were laporatomized under anesthesia to excise two-thirds of the liver according to the method described by Higgins and Anderson (1931). These rats were bled 24, 36, 48 and 72 hours after hepatectomy, bled the liver was removed, 2 g of the liver was homogenized in ice water by adding 0.05M Tris-HCl buffer containing 0.005M cooled 2-mercaptoethanol (pH 8.0) in 4-fold volume of the liver. The homogenate was centrifuged at 1,000 xg for 30 min. The resultant supernatant was used as an enzyme solution, which was determined for the activity of important enzyme groups responsible for DNA synthesis. Thymidine kinase activity was determined by the Bresnick and Karjala method (1964), dCMP deaminase activity was determined by the combined methods of Maley et al. (1964) and Gullen et al. (1978), and CTP synthetase activity was determined by the modified method of Williams et al. (1978). The enzyme activities of the injected groups were compared with those in the controls. The resuls are shown in Table 7. Twenty-four hours after partial hepatectomy, the thymidine kinase activity, the dCMP deaminase activity and the CTP synthetase activity in the WHS-injected groups increased about 8 fold, 3.2 fold and 1.4 fold, respectively, as compared with those in the control groups.

The activity was markedly higher in the WHS-injected groups than in the control groups during a short time of period after hepatectomy, but the difference became smaller with the passage of time, and no significant difference was found between the groups 72 hours later. Induction of these enzyme activities were not observed in the control group. The results suggest that WHS has an action to further stimulate regenerated liver DNA synthesis by hepatectomy.

EXPERIMENT 2

One ml of 0.02–0.05% solution of WHS containing isotonic saline alone were injected intraperitoneally into groups of 10 SPF-Wister strain male rats each weighing 150 g. A control group of ten rats (each weighing approximately 150 g) was injected with an isotonic saline solution. Two-thirds of the liver was removed 12 hours after injection. Ninety-six hours after surgery the rats were sacrificed and bled. The livers were removed from the rats, and wet weights were determined. The wet weights of the livers were divided by the body weights and the liver-body weight indices (L/B indices) calculated. As shown in Table 8, injected with WHS solution had higher L/B indices than the control group.

The above results suggest that WHS has an action to stimulate the DNA synthesis and maturation of the hepatic cells of the partially hepatectomyzed rat liver.

TABLE 7

Effects of post-injection of WHS on various enzyme activities of rat regenerating liver

| | Doses mg/body weight | Time after hepatectomy (hrs) | enzyme activities (nmol/mg protein/30 min) control group | treated group |
|---|---|---|---|---|
| Thymidine kinase | 0.2 | 24 | 0.41 ± 0.27 | 1.09 (n = 3) |
| | 1.0 | 24 | 0.41 ± 0.27 | 3.00 ± 2.63 |
| | 5.0 | 24 | 0.41 ± 0.27 | 3.27 ± 1.75 |
| | 5.0 | 36 | 4.77 ± 0.21 | 6.99 ± 2.11 |
| | 5.0 | 72 | 3.50 ± 0.79 | 4.66 ± 1.67 |
| | 5.0 | 24 | 0.44 ± 0.05 | 0.62 ± 0.06 |
| CTP synthetase | 5.0 | 72 | 1.21 ± 0.29 | 1.13 ± 0.13 |
| dCMP deaminase | 5.0 | 24 | 2.22 ± 0.71 | 7.10 ± 2.44 |

TABLE 8

Effects of pre-injected WHS on increased weights of rat regenerated liver

| Treatment | Liver weight 96 hours after hepatectomizing liver (Liver weight/body weight) Exp. - 1 | Exp. - 2 |
|---|---|---|
| control group (isotonic saline) | 0.030 ± 0.002 (n = 8) | 0.031 ± 0.001 (n = 7) |
| WHS injected group | 0.035 ± 0.003 (n = 8) | 0.035 ± 0.002 (n = 7) |

THERAPEUTIC EFFECT OF THE SUBSTANCE IN THE PRESENT INVENTION ON EXPERIMENTALLY INDUCED WOUNDS

The above mentioned finding may anticipate the effectiveness of the substance in the present invention not only for cell levels but also for healing of wounds. Hyperplasia of the granulation tissue and formation on the epidermis indicates stimulation or maturation of growth of fibroblasts and epidermal cells, which were satisfactorily verified by tissue-culturing experiment.

The inventors demonstrated the more excellent wound-healing effectiveness of substance than that of presently-used wound treatment agents by experimentally injuring the rat backs and observing the therapeutic effect of the substance. We here firmly believed the providability of new wound treatment agent.

The wound healing experiment was carried out by the following method using groups of 10 Wistar strain male rats. Hair on the back of the rats was clipped with a pair of hair clippers. After ether-anesthetized, the rats were laid, and their skin was punched with a chisel of a diameter of 13 mm from the left to right with their skin held between one's fingers along the median line. Immediately after formation of the wounds, the areas of the wounds were determined once a day and the time-course decrease in the wound areas was indicated in terms of the percentage of the areas on the first day. The rats received application of ointment of the substance in a dose of 100 mg per the wounded portion twice a day.

The wounded surfaces were kept open until the exfoliation of the crust. Rat shackles were fixed at the rear of the forelegs preventing the rats from licking the wounded surfaces.

The substance in the present invention (WHS) in amounts of 25, 50, 100, 200, 400 and 800 mg was added to each 1 kg of petrolatum to make ointments, which were used for the wound healing experiment. Addition of 25–250 mg WHS to 1 kg vaseline was found to display satisfactory wound healing effectiveness.

WHS displayed marked wound healing effectiveness in the copresence of zinc oxide. The optimum concentration of zinc oxide ointment containing WHS was determined for wound treating effectiveness.

Addition of WHS to petrolatum ointments containing 10% and 20% zinc oxide showed the most preferable wound treating effectiveness. Although an unsteady phase was usually present at the beginning of wounding, at the point which the wounded portion enlarged temporarily, administration of 250 mg WHS-containing 20% zinc oxide-petrolatum ointment to the portion was found to suppress the unsteady phase to promote the healing effectively. Histological examination clearly showed, as compared with the control group, earlier maturation of fibroblasts in the tissues and also satisfactory formation of the epidermis.

Table 9 shows the comparison of effectiveness of therapeutic agents which are at present used clinically.

As shown in Table 9, WHS ointment showed more significant therapeutic effectiveness than petrolatum ointment free of any drugs, and the effectiveness was found to be nearly the same as that of therapeutic agents at present clinically used. However, addition of 20% zinc oxide to WHS ointment displayed more marked wound healing effectiveness than the agents at present clinically used, with the proviso that zinc oxide ointment alone displayed no effectiveness.

WHS ointment containing 1–10% by weight of zinc stearate showed intermediate wounded-treating effectiveness between WHS ointment and WHS-zinc ointment.

The presence of the wound healing effectiveness of epidermal growth factor (EGF) was investigated. As shown in Table 10, no difference in effectiveness was observed between the EGF-containing ointment and petrolatum ointment, and EGF was therefore found to be unexpectable as a wound-treating agent.

TABLE 9

Comparison of wound therapeutic effect

| Ointment | Therapeutic effect (ratio of wound area %) days 0 | 1 | 2 | 3 | 4 | 5 | 6 | 7 |
|---|---|---|---|---|---|---|---|---|
| Base ointment | 100 | 131.39 ± 4.63 | 118.84 ± 3.05 | 112.20 ± 3.73 | 104.21 ± 3.58 | 93.44 ± 2.92 | 70.29 ± 3.23 | 49.14 ± 3.09 |
| ZnO ointment | 100 | 124.65 ± 4.07 | 123.48 ± 3.57 | 119.81 ± 5.90 | 108.14 ± 4.82 | 95.96 ± 4.80 | 69.97 ± 3.10 | 52.67 ± 3.25 |
| WHS ointment | 100 | 125.17 ± 4.24 | 103.15** ± 3.57 | 101.41* ± 3.80 | 95.93 ± 3.35 | 73.80*** ± 3.90 | 50.48*** ± 3.25 | 34.50** ± 2.77 |
| WHS-ZnO ointment | 100 | 123.91 ± 3.84 | 101.07*** ± 3.47 | 93.02*** ± 4.24 | 82.48*** ± 3.72 | 62.82*** ± 2.90 | 39.60*** ± 1.91 | 23.22*** ± 1.51 |
| A ointment | 100 | 130.25 ± 4.52 | 120.88 ± 4.13 | 118.56 ± 5.70 | 102.76 ± 3.58 | 82.92 ± 2.51 | 63.25 ± 1.94 | 36.22** ± 1.27 |
| B ointment | 100 | 121.33 ± 4.20 | 115.73 ± 4.49 | 113.91 ± 5.40 | 102.41 ± 5.02 | 88.90 ± 3.63 | 63.19 ± 3.11 | 40.07* ± 2.35 |
| C ointment | 100 | 134.40 ± 4.64 | 127.83 ± 4.77 | 125.76 ± 5.28 | 116.30 ± 3.93 | 98.84 ± 3.93 | 64.50 ± 3.50 | 37.67** ± 2.21 |

| Ointment | Therapeutic effect (ratio of wound area %) days 8 | 9 | 10 | 11 | 12 | 13 | 14 | 15 |
|---|---|---|---|---|---|---|---|---|
| Base ointment | 35.51 ± 2.54 | 21.01 ± 1.66 | 12.69 ± 0.85 | 8.42 ± 0.57 | 4.93 ± 0.53 | 1.95 ± 0.42 | 0.44 ± 0.18 | 0.27 ± 0.15 |
| ZnO ointment | 37.15 ± 2.52 | 24.33 ± 2.15 | 15.71 ± 1.77 | 10.54 ± 1.57 | 5.94 ± 1.21 | 4.39 ± 1.05 | 2.08 ± 0.72 | 1.32 ± 0.49 |
| WHS ointment | 23.53*** ± 1.99 | 15.91* ± 1.31 | 10.03* ± 0.96 | 11.34 ± 1.73 | 4.38 ± 0.82 | 2.70 ± 0.70 | 1.03 ± 0.40 | 0.61 ± 0.29 |
| WHS-ZnO ointment | 16.22*** ± 1.60 | 11.04*** ± 1.30 | 6.46*** ± 1.12 | 4.03** ± 0.97 | 2.09** ± 0.61 | 0.72** ± 0.34 | 0.05** ± 0.04 | 0 |
| A ointment | 23.63*** ± 1.43 | 15.33** ± 0.89 | 9.49** ± 0.81 | 6.21* ± 0.79 | 4.69 ± 0.77 | 2.41 ± 0.57 | 0.98 ± 0.32 | 0.66 ± 0.31 |
| B ointment | 26.04 ± 1.70 | 17.87 ± 1.27 | 12.30 ± 1.17 | 8.86 ± 1.10 | 6.07 ± 0.85 | 3.81 ± 0.75 | 1.82 ± 0.53 | 1.47 ± 0.68 |
| C ointment | 23.80** ± 1.71 | 16.25* ± 1.53 | 9.48* ± 0.89 | 5.39** ± 0.72 | 2.74* ± 0.66 | 1.48 ± 0.49 | 0.54 ± 0.23 | 0.35 ± 0.18 |

Mean ± S.E. n = 10
*P < 0.05
**P < 0.01
***P < 0.001
A Ointment contains young bovine whole blood deproteinized extract as the active ingredient
B Ointment contains fibrinolidine and deoxyribonuclease as the active ingredient
C Ointment contains (1-benzyl-1H—indazol-3-yl)oxy acetic acid as the active ingredient

TABLE 10

Comparison of wound therapeutic effect

| ointment | Therapeutic effect (ratio of wound area %) days 0 | 1 | 2 | 3 | 4 | 5 | 6 | 7 |
|---|---|---|---|---|---|---|---|---|
| Base ointment | 100 | 121.34 ± 5.96 | 117.91 ± 4.91 | 103.02 ± 4.49 | 96.12 ± 3.43 | 86.88 ± 3.24 | 69.20 ± 3.52 | 51.26 ± 4.73 |

TABLE 10-continued

| Comparison of wound therapeutic effect | | | | | | | | |
|---|---|---|---|---|---|---|---|---|
| EGF ointment | 100 | 115.73 ± 3.96 | 115.55 ± 1.84 | 100.76 ± 2.73 | 94.62 ± 2.00 | 82.11 ± 2.34 | 62.17 ± 1.78 | 45.80 ± 2.54 |

| | Therapeutic effect (ratio of wound area %) days | | | | | | | |
|---|---|---|---|---|---|---|---|---|
| ointment | 8 | 9 | 10 | 11 | 12 | 13 | 14 | 15 |
| Base ointment | 38.42 ± 4.12 | 23.42 ± 2.94 | 13.79 ± 1.53 | 8.14 ± 0.91 | 3.71 ± 0.42 | 1.50 ± 0.34 | 0.44 ± 0.16 | 0.14 ± 0.10 |
| EGF ointment | 34.49 ± 2.92 | 20.63 ± 1.24 | 10.98 ± 1.19 | 6.94 ± 0.71 | 4.14 ± 0.68 | 1.70 ± 0.45 | 0.99 ± 0.43 | 0.26 ± 0.18 |

Mean ± S.E. n = 10

ACTION OF WHS ON EXPERIMENTALLY INDUCED STRESS-DERIVED ULCER EXPERIMENT 1

Groups of 5 SPF-Wistar strain rats weighing 180 g were fasted for 16 hours. One ml of 1%, 5%, and 10% solution of WHS containing isotonic saline was injected into the stomach of the animals from their mouths using an oral probe. For the control group 5 animals of the same were subjected to the same pretreatment, then 1 ml of isotonic saline alone was administered by the same method. Then the rats of the two groups were placed in the respective stress cages. The stress cages were immersed in a water bath maintained at 23° C. until their chests reached the water level. After such conditions had been continued for 16 hours, the rats were uncaged, sacrificed at once, and laparotomized. The junction of the stomach and the jejunum was tightly knotted with sewing cotton, the jejunum was cut and the portion between the preventriculus and the esophagus was also cut to pull out the stomach. Ten ml of 10% formalin solution was injected into the cut portion of the preventricular, which was also tightly knotted with sewing cotton. The stomach which was pulled out was immersed into the formalin solution for 10 minutes. Afterward the stomach was drawn from the solution, and its external curved portion was sliced. The inside of the stomach was rinsed with water to remove the blood clots. The stomach was shaped into a plate-like matter to measure the lengths of linear ulcers with the total length represented by stress-induced ulcer indices (mm). No significant difference was found between the control groups and the WHS-added groups indicating that no preventive effect was observed for the development of stress-induced ulcers.

EXPERIMENT 2

Respective 5 rats in treating groups and control groups, each rat being kept fasting for 16 hours, were placed in one stress cage for every group. The cages were immersed in a water bath maintained at 23° C. and the rats were uncaged 16 hours later. The treating animals received 1 ml Of 0.5% WHS-containing isotonic saline once everyday since the day of uncaging by the same method as described in Experiment 1. The rats were sacrificed 1, 2, and 3 days after formation of ulcers (the day immediately after formation of ulcer was taken as 0 day), and bled. Then the stomach was pulled out and treated by the same method as discribed in Experiment 1 to obtain stress-induced ulcer indises. Animals in the control groups received 1 ml of isotonic saline. As shown in Table 11, the stress-derived ulcer indises in the WHS-administered groups were siginificantly smaller than those in the control group. For this reason, WHS was found to have an action to promote the healing of experimentally induced stress-derived ulcers.

TABLE 11

Healing effectiveness of WHS on experimentally induced stress-derived ulcers

| Number of days after formation of ulcers | Degree of ulcers (ulcer index: mm) WHS-administered group | control group |
|---|---|---|
| 0-th day | — | 76.0 ± 13.5 |
| 1st day | 40.6 ± 18.7 | 73.1 ± 12.0 |
| 2nd day | 32.2 ± 16.2 | 65.2 ± 18.1 |
| 3rd day | 26.6 ± 5.3 | 42.4 ± 15.1 |

number of rats used: 15-20

SIDE EFFECTS-PREVENTING ACTION OF STEROIDS

Steroids, although pharmaceutical preparations are presently used extensively in clinical treatment, have many side effects, requiring careful administration.

Berlinger and Ruhman (J. Invest. Derm. 49, 117-122, 1967) have pointed out that antiinflammatory steroids such as cortisol and fluocinolone acetanide inhibited growth of incubated mouse fibroblasts, bringing about morphological changes such as protoplasmic vacuolation.

The results indicated that the clinical effectiveness of anti-inflammatory steroids was in agreement with the in vitro fibroblast-inhibitory activity of glucosteroids. The use of glucosteroids sometimes caused cutaneous atrophy.

Asoo et al. (J. of Jap. Derm. Ass.: 90, 7, 599-604, 1980) investigated the in vitro fibroblast inhibitory activity of external glucosteroids and reported that incubated human cutaneous fibroblasts were inhibited by clobetasol-17-propionate, betamethasonedipropionate, hydrocortisone-butylate, betamethasone-17-valerate, and hydrocortisone in the descending order. They have observed that clobetasol-17-propionate especially caused human fibroblastic nuclei and protoplasms to denature in an amount of 25 μg/ml.

The inventors determined the concentrations of various steroids (hydrocortisone, predonisolone, dexamethasone, and fluocinolone acetanide) which inhibit fibroblasts (refer to Table 12). As shown in Table 13, 14, 15, and 16, we confirmed that addition of WHS to steroids, which inhibited cell growth by 50%, decreased the inhibitory activity of the steriods depending on the concentration of WHS added, thus eliminating nucleic acid protoplasmic denaturation.

It means that WHS exerts very important activity on the prevention of externally used steroids-derived side effects. In view of the findings, we belive firmly that new side effects-free external steroids containing WHS (including addition of WHS to steroid preparations at present available) can be provided.

TABLE 12

| Steroids | Doses | Inhibitory effects of BHK-21 cells: cell numbers × $10^5$ cells/dish | % | cell numbers × $10^5$ cells/dish | % | cell numbers × $10^5$ cells/dish | % |
|---|---|---|---|---|---|---|---|
| | | days: 2 | | 4 | | 6 | |
| Hydrocortisone | control | 12.4 | 100.0 | 25.9 | 100.0 | 26.0 | 100.0 |
| | 0.5 μg/ml | 13.0 | 104.8 | 24.0 | 92.7 | 25.6 | 98.5 |
| | 1.0 μg/ml | 12.5 | 100.8 | 23.8 | 91.7 | 25.1 | 96.5 |
| | 5.0 μg/ml | 12.0 | 96.8 | 21.9 | 84.6 | 25.2 | 96.9 |
| | 25.0 μg/ml | 9.3 | 75.0 | 17.1 | 66.0 | 22.6 | 86.9 |
| | 50.0 μg/ml | 8.2 | 66.1 | 10.8 | 41.7 | 10.0 | 40.0 |
| Dexamethasone | control | 0.97 | 100.0 | 2.26 | 100.0 | 2.58 | 100.0 |
| | 0.5 μg/ml | 0.92 | 94.8 | 2.32 | 87.2 | 2.51 | 97.3 |
| | 1.0 μg/ml | 0.87 | 89.7 | 2.31 | 86.8 | 2.54 | 98.4 |
| | 5.0 μg/ml | 0.84 | 86.6 | 2.22 | 83.5 | 2.57 | 99.6 |
| | 25.0 μg/ml | 0.71 | 73.2 | 1.71 | 64.3 | 2.33 | 90.3 |
| | 50.0 μg/ml | 0.62 | 63.9 | 1.24 | 46.6 | 1.84 | 71.3 |
| Prednisolone | control | 1.31 | 100.0 | 2.72 | 100.0 | 2.65 | 100.0 |
| | 0.5 μg/ml | 1.20 | 91.6 | 2.43 | 89.3 | 2.51 | 94.7 |
| | 1.0 μg/ml | 1.20 | 91.6 | 2.45 | 90.1 | 2.50 | 94.3 |
| | 5.0 μg/ml | 1.09 | 83.2 | 2.33 | 85.7 | 2.48 | 93.6 |
| | 25.0 μg/ml | 0.85 | 64.9 | 1.49 | 54.8 | 1.91 | 72.1 |
| | 50.0 μg/ml | 0.73 | 55.7 | 1.01 | 37.1 | 0.98 | 37.0 |
| | | days: 1 | | 3 | | 5 | |
| Fluocinolone acetanide | control | 0.14 | 100.0 | 1.34 | 100.0 | 2.19 | 100.0 |
| | 0.5 μg/ml | 0.15 | 107.1 | 1.16 | 86.6 | 1.66 | 75.8 |
| | 1.0 μg/ml | 0.15 | 107.1 | 1.04 | 77.6 | 1.72 | 78.5 |
| | 5.0 μg/ml | 0.15 | 107.1 | 1.02 | 76.1 | 1.66 | 75.8 |
| | 25.0 μg/ml | 0.15 | 107.1 | 0.88 | 65.7 | 1.39 | 63.5 |
| | 50.0 μg/ml | 0.12 | 85.7 | 0.71 | 53.0 | 1.12 | 51.1 |

TABLE 13

Effects of WHS on BHK-21 cells in the presence of Hydrocortisone

| conditions | cell numbers (×$10^5$ cells/dish) culture: 2nd days | 4th days |
|---|---|---|
| control | 14.2 | 27.4 |
| Hydrocortisone 50 μg/ml | 8.2 | 12.6 |
| Hydrocortisone 50 μg/ml + WHS 25 μg/ml | 12.2 | 19.2 |
| Hydrocortisone 50 μg/ml + WHS 50 μg/ml | 13.6 | 21.4 |
| Hydrocortisone 50 μg/ml + WHS 100 μg/ml | 16.0 | 24.3 |
| Hydrocortisone 50 μg/ml + WHS 200 μg/ml | 18.9 | 27.7 |

TABLE 14

Effects of WHS on BHK-21 cells in the presence of Dexamethasone

| conditions | cell numbers (× $10^5$ cells/dish) culture: 2nd days | 4th days |
|---|---|---|
| control | 1.56 | 2.51 |
| Dexamethasone 50 μg/ml | 0.87 | 1.28 |
| Dexamethasone 50 μg/ml + WHS 50 μg/ml | 1.20 | 1.70 |
| Dexamethasone 50 μg/ml + WHS 100 μg/ml | 1.35 | 1.93 |
| Dexamethasone 50 μg/ml + WHS 200 μg/ml | 1.58 | 2.16 |
| Dexamethasone 50 μg/ml + WHS 400 μg/ml | 1.61 | 2.39 |

TABLE 15

Effects of WHS on BHK-21 cells in the presence of Prednisolone

| conditions | cell numbers (× $10^5$ cells/dish) culture: 2nd days | 4th days |
|---|---|---|
| control | 1.56 | 2.51 |
| Prednisolone 50 μg/ml | 0.78 | 0.94 |
| Prednisolone 50 μg/ml + WHS 50 μg/ml | 1.05 | 1.35 |
| Prednisolone 50 μg/ml + WHS 100 μg/ml | 1.22 | 1.50 |
| Prednisolone 50 μg/ml + WHS 200 μg/ml | 1.42 | 1.84 |
| Prednisolone 50 μg/ml + WHS 400 μg/ml | 1.82 | 2.43 |

TABLE 16

Effects of WHS on BHK-21 cells in the presence of Fluocinolone acetanide

| conditions | cell numbers (× $10^5$ cells/dish) culture: 3rd days | 5th days |
|---|---|---|
| control | 1.50 | 2.09 |
| Fluocinolone acetanide 50 μg/ml | 0.97 | 1.22 |
| Fluocinolone acetanide 50 μg/ml + WHS 25 μg/ml | 1.28 | 1.43 |
| Fluocinolone acetanide 50 μg/ml + WHS 50 μg/ml | 1.36 | 1.48 |
| Fluocinolone acetanide 50 μg/ml + WHS 100 μg/ml | 1.45 | 1.64 |
| Fluocinolone acetanide 50 μg/ml + WHS 200 μg/ml | 1.80 | 1.98 |

OTHERS

Mutagenicity: When mutagenicity testing was performed using V-79 cells, no induced mutagenicity due to the substance in the present invention was observed.

Toxicity: Crj: Toxicity was observed for 14 days after administration of the substance (WHS) to 6-week-old CD strain SPF rats of groups made up of 10 males or 10 females. $LD_{50}$'s and 95% confidence limits were obtained by the Probit method dependent upon mortality in the respective dose groups to give the following results.

| Route | Sex | $LD_{50}$ (95% confidence Limit) mg/kg |
|---|---|---|
| p.o. | Male | >2000 |
| | Female | >2000 |
| s.c. | Male | >2000 |
| | Female | >2000 |
| i.v. | Male | 356 (303–407) |
| | Female | 498 (433–578) |

The following are examles of formulations containing the cell growth-stimulating substance in the present invention (WHS).

WHS Ointment:

Fifty grams of purified lanolin, 50 g of white bees wax, and 900 g petrolatum were blended with a kneading machine while warming them to prepare the base I, which was allowed to cold to room temperature. To 1 kg of the base I was added 0.25 g of WHS dissolved in 10 ml of sterilized distilled water, and the mixture was kneaded to prepare WHS Ointment.

WHS-Zinc Ointment:

Zinc oxide, 200 g, was kneaded with 70 g of purified lanolin, to which 730 g of the above base (I) was added. The blend was again kneaded while warming to prepare the base (II) which was allowed to cool to room temperature. To 1 kg of the base (II) was added 0.25 g of WHS dissolved in 10 ml of sterilized distilled water to give WHS-Zinc Oxide Ointment.

WHS-Zinc Stearate Ointment:

Zinc stearate, 50 g, was kneaded with 70 g of purified lanolin, to which 880 g of base (I) was added. The blend was again kneaded while warming to prepare the base (II), which was allowed to cool to room temperature. To 1 kg of the base (II) was added 0.25 g of WHS dissolved in 10 ml of sterilized distilled water to give WHS-Zinc Stearate Ointment.

A liquid, emulsion, capsule, and tablet each containing WHS having the following compositions were prepared according to conventional method.

| | |
|---|---|
| (I) Composition of the cosmetic water-type liquid | |
| Polyoxyethylene-hardened Castor Oil | 1.0 |
| Ethanol | 13.0–15.0 |
| Methyl p-Hydroxybenzoate | 0.1 |
| Citric Acid | 0.1 |
| Sodium Citrate | 0.1–0.3 |
| 1,3-Butylene Glycol | 2.0–4.0 |
| WHS | 0.05 |
| Purified Water | q.s. |
| (II) Composition of the emulsion | |
| Polyoxyehylene Monopalmitate | 1.0–1.5 |
| Tetraoleic Acid | 0.8–0.5 |
| Monostearic Acid | 1.5–1.0 |
| Stearic Acid | 0.8–0.3 |
| Ceresin | 0.3 |
| Cetyl Alcohol | 1.0–1.5 |
| Vegetable Oil | 5.0–3.0 |
| Fat and Oil | 5.0 |
| Ethyl p-Hydroxybenzoate | 0.1 |
| 1,3-Butylene Glycol | 7.0 |
| WHS | 0.05 |
| Purified Water | q.s. |
| (III) Composition of the Capsule | |
| Lactose | 40 |
| Crystalline Cellulose | 15 |
| Calcium Stearate | 15 |
| Talc | 30 |

-continued

| | |
|---|---|
| WHS | 0.01 |
| (IV) Composition of the Tablet | |
| Lactose | 40 |
| 3% HPC Lactose | 30 |
| Crystalline Cellulose | 20 |
| Potato Starch | 8 |
| Talc Stearate | 2 |
| (A 1:1 mixture of magnesium stearate and talc). | |
| WHS | 0.01 |
| Purified Water | q.s. |

What is claimed is:

1. A protein having cell growth stimulating activity, said protein selected from those obtained from a culture of a microorganism selected from the group consisting of *Staphylococcus epidermidis, Bacillus subtilis, Streptococcus faecalis, Serratia marcescens, Escherichia coli, Salmonella enteritidis,* and *Proteus vulgaris,* the protein being characterized as follows:

(a) Molecular weight in the range of 5,000–12,000, when said molecular weight is calculated on the basis of a calibration curve plotting the relationship between the molecular weight and an amount eluted by high performance liquid chromatography using as marker proteins, thioglobin (M.W. 670,000), bovine γ-globulin (M.W. 158,000), fowl ovalbumin (M.W. 44,000), equine myoglobulin (M.W. 17,000), and vitamin B-12 (M.W. 1,350);

(b) Ultraviolet absorption at 278 nm;

(c) Infrared absorption spectrum with dominant peaks at 1300, 1550, and 1630 $cm^{-1}$;

(d) Isoelectric point in the range of 4.0–6.6;

(e) Soluble in water and insoluble in methanol, ethanol, acetone and ether;

(f) Appears as a grayish white powder in the lyophilized state;

(g) Positive for the following color reactions; Xanthoprotein, Pauli, Sakaguchi, Hunter, Sullivan, Hopkins-Cove, nitrosonaphthol, Millon, Neubauer-Road, and Libermann; and (h)

| Amino Acid | mol/M |
|---|---|
| Aspartic Acid | 4.25–14.33 |
| Glutamic Acid | 4.76–21.35 |
| Glycine | 3.68–10.04 |
| Valine | 3.05–8.97 |
| Alanine | 3.51–18.09 |
| Threonine | 2.20–5.69 |
| Serine | 2.01–5.14 |
| Cystine | 0.00–0.40 |
| Methionine | 0.79–2.73 |
| Isoleucine | 2.34–7.97 |
| Leucine | 2.70–8.70 |
| Tyrosine | 0.39–3.17 |
| Phenylalanine | 0.79–3.20 |
| Lysine | 2.22–8.80 |
| Histidine | 0.54–1.35 |
| Arginine | 0.65–4.83 |
| Proline | 2.63–5.37 |
| Tryptophan | 0.25–0.70 |

said protein exhibiting cell growth stimulating activity in a pH range between 4–10; and being substantially free of nucleoside phosphotransferase.

2. A composition for stimulating cell growth comprising the protein of claim 1 as an active ingredient, and a pharmaceutically acceptable carrier.

3. The composition according to claim 2, wherein the carrier is an ointment.

4. The composition according to claim 3, wherein the protein is present in an amount of about 0.0025–0.25 percent by weight.

5. The composition according to claim 2, and further comprising a zinc compound.

6. The composition according to claim 5, and wherein said zinc compound is selected from the group consisting of zinc oxide and zinc salts of fatty acids.

7. The composition according to claim 6, wherein the zinc compound is zinc oxide, and the ratio of protein to zinc oxide is in the range of from 1:2000 to 1:8000, calculated on the basis of percent by weight.

8. The composition according to claim 6, and wherein the zinc compound is a zinc salt of a fatty acid, and the ratio of protein to zinc salt of fatty acid, is in the range of from 1:400 to 1:4000, calculated on the basis of percent by weight.

9. The composition according to claim 2, and further comprising an adrenal cortical hormone.

10. The composition according to claim 9, and wherein the ratio of protein to adrenal cortical hormone is from 1:1 to 1:10, calculated on the basis of percent by weight.

11. A protein having cell growth stimulating activity, said protein selected from those obtained from a culture of a microorganism selected from the group consisting of *Staphylococcus aureus, Sarcina lutea, Aerococcus viridians, Acinetobacter calcoaceticus, Corynebacterium fascians,* and *Clostridium perfringens;* the protein being characterized as follows:

(a) Molecular weight in the range 10,000–15,000, when said molecular weight is calculated on the basis of a calibration curve plotting the relationship between the molecular weight and an amount eluted by high performance liquid chromatography using as marker proteins, thioglobin (M.W. 670,000), bovine γ-globulin (M.W. 158,000), fowl ovalbumin (M.W. 44,000), equine myoglobin (M.W. 17,000), and vitamin B-12 (M.W. 1,350);

(b) Ultraviolet absorption at 278 nm;

(c) Infrared absorption spectrum with dominant peaks at 1300, 1550, and 1630 $cm^{-1}$;

(d) Soluble in water and insoluble in methanol, ethanol, acetone and ether;

(e) Appears as a grayish white powder in the lyophilized state;

(f) Positive for the following color reactions: Xanthoprotein, Pauli, Sakaguchi, Hunter, Sullivan; Hopkins-Cole, nitrosonaphthol, Millon, Neubauer-Road, and Liebermann;

(g) Isoelectric point in the range of 4.0–5.5; and (h)

| Amino Acid | mol/M |
|---|---|
| Aspartic Acid | 9.65–18.78 |
| Glutamic Acid | 12.36–43.08 |
| Glycine | 6.71–11.78 |
| Valine | 6.43–12.16 |
| Alanine | 8.07–14.68 |
| Threonine | 4.60–7.72 |
| Serine | 4.56–11.45 |
| Cystine | 0.00 |
| Methionine | 1.46–2.86 |
| Isoleucine | 3.98–6.77 |
| Leucine | 4.97–8.13 |
| Tyrosine | 0.62–2.63 |
| Phenylalanine | 1.75–3.44 |

-continued

| Amino Acid | mol/M |
|---|---|
| Lysine | 4.53–8.95 |
| Histidine | 1.04–1.78 |
| Arginine | 0.80–2.33 |
| Proline | 4.27–12.69 |
| Tryptophan | 0.32–0.63 |

said protein being substantially free of nucleoside phosphotransferase.

12. A composition for stimulating cell growth comprising the protein of claim 11 as an active ingredient, and a pharmaceutically acceptable carrier.

13. The composition according to claim 12, wherein the carrier is an ointment.

14. The composition according to claims 13, wherein the protein is present in an amount of about 0.0025–0.25 percent by weight.

15. The composition according to claim 12, and further comprising a zinc compound.

16. The composition according to claim 15, and wherein said zinc compound is selected from the group consisting of zinc oxide and zinc salts of fatty acids.

17. The composition according to claim 16, wherein the zinc compound is zinc oxide and the ratio of protein to zinc oxide is in the range of from 1:2000 to 1:8000, calculated on the basis of percent by weight.

18. The composition according to claim 16, and wherein the zinc compound is a zinc salt of a fatty acid and the ratio of protein to zinc salt of fatty acid is in the range of from 1:400 to 1:4000, calculated on the basis of percent by weight.

19. The composition according to claim 12, and further comprising an adrenal cortical hormone.

20. The composition according to claim 19, and wherein the ratio of protein to adrenal cortical hormone is from 1:1 to 1:10, calculated on the basis of percent by weight.

21. A protein having cell growth stimulating activity, said protein selected from those obtained from a culture of the microorganism *Clostridium perfringens,* the protein being characterized as follows:

(a) Molecular weight of 150,000–160,000, when said molecular weight is calculated on the basis of a calibration curve plotting the relationship between the molecular weight and an amount eluted by high performance liquid chromatography using as marker proteins, thioglobin (M.W. 670,000), bovine γ-globulin (M.W. 158,000), fowl ovalbumin (M.W. 44,000), equine myoglobulin (M.W. 17,000), and vitamin B-12 (M.W. 1,350); and a molecular weight of approximately 53,000, when determined by SDS disk electrophoresis;

(b) Ultraviolet absorption at 278 nm;

(c) Infrared absorption spectrum with dominant peaks at 1300, 1550, and 1630 $cm^{-1}$;

(d) Soluble in water and insoluble in methanol, ethanol, acetone and ether;

(e) Appears as a grayish white powder in the lyophilized state;

(f) Positive for the following color reactions: Xanthoprotein, Pauli, Sakaguchi, Hunter, Sullivan; Hopkins-Cole, nitrosonaphthol, millon, Neubauer-Road, and Liebermann; and (g)

| Amino Acid | mol/M |
|---|---|
| Aspartic Acid | 109.80 |
| Glutamic Acid | 96.18 |
| Glycine | 71.66 |
| Valine | 73.01 |
| Alanine | 73.69 |
| Threonine | 40.39 |
| Serine | 45.59 |
| Cystine | 2.92 |
| Methionine | 16.56 |
| Isoleucine | 54.64 |
| Leucine | 65.42 |
| Tyrosine | 54.29 |
| Phenylalanine | 27.43 |
| Lysine | 75.66 |
| Histidine | 10.48 |
| Arginine | 21.37 |
| Proline | 32.55 |
| Tryptophan | 3.36 |

said protein being substantially free of nucleoside phosphotransferase.

22. A composition for stimulating cell growth comprising the protein of claim 21 as an active ingredient, and a pharmaceutically acceptable carrier.

23. The composition according to claim 22, wherein the carrier is an ointment.

24. The composition according to claim 23, wherein the protein is present in an amount of about 0.0025–0.25 percent by weight.

25. The composition according to claim 22, and further comprising a zinc compound.

26. The composition according to claim 25, and wherein said zinc compound is selected from the group consisting of zinc oxide and zinc salts of fatty acids.

27. The composition according to claim 26, wherein the zinc compound is zinc oxide and the ratio of protein to zinc oxide is in the range of from 1:2000 to 1:8000, calculated on the basis of percent by weight.

28. The composition according to claim 26, and wherein the zinc compound is a zinc salt of a fatty acid and the ratio of protein to zinc salt of fatty acid is in the range of from 1:400 to 1:4000, calculated on the basis of percent by weight.

29. The composition according to claim 22, and further comprising an adrenal cortical hormone.

30. The composition according to claim 29, and wherein the ratio of protein to adrenal cortical hormone is from 1:1 to 1:10, calculated on the basis of percent by weight.

* * * * *